United States Patent [19]

Noda

[11] Patent Number: 5,397,362
[45] Date of Patent: Mar. 14, 1995

[54] IMPLANT PROSTHESIS AND METHOD FOR PRODUCING SAME

[75] Inventor: Iwao Noda, Shiga, Japan

[73] Assignee: Kyocera Corporation, Kyowa, Japan

[21] Appl. No.: 127,422

[22] Filed: Sep. 27, 1993

Related U.S. Application Data

[63] Continuation of Ser. No. 851,256, Mar. 13, 1992, abandoned, which is a continuation of Ser. No. 544,843, Jun. 27, 1990, abandoned.

[30] Foreign Application Priority Data

Jun. 30, 1989 [JP] Japan .................................. 1/170950

[51] Int. Cl.⁶ .............................................. A61F 2/28
[52] U.S. Cl. ...................................... 623/16; 433/201.1
[58] Field of Search .................. 623/16, 18; 433/201.1

[56] References Cited

U.S. PATENT DOCUMENTS

| | | | |
|---|---|---|---|
| 4,259,072 | 3/1981 | Hirabayashi et al. | 623/16 |
| 4,366,253 | 12/1982 | Yagi | 623/16 |
| 4,483,678 | 11/1984 | Nishio et al. | 623/18 |

FOREIGN PATENT DOCUMENTS

| | | | |
|---|---|---|---|
| 0264917 | 4/1988 | European Pat. Off. | 623/16 |
| 0324143 | 7/1989 | European Pat. Off. | 623/18 |
| 2378733 | 9/1978 | France | 623/16 G |

*Primary Examiner*—Randy C. Shay
*Attorney, Agent, or Firm*—Spensley Horn Jubas & Lubitz

[57] ABSTRACT

An implant prosthesis comprising implant substrate of ceramic material, a thin glass layer coated over the adhering interface of the substrate relative at least to a bone, and a thermally sprayed layer of calcium phosphate based material formed over the glass layer.

The implant provides excellent adhesion of the thermally sprayed layer of calcium phosphate based material to the substrate, with ensuring advantages of stabilized implantation in a living body in that the thin glass layer between the substrate and the calcium phosphate based material removes fear of the sprayed material coming off and/or falling off the substrate or possibility of bringing about reduced strength of the substrate.

8 Claims, 1 Drawing Sheet

IMPLANT PROSTHESIS AND METHOD FOR PRODUCING SAME

This is a continuation of application Ser. No. 07/851,256, filed on Mar. 13, 1992, now abandoned, which is a continuation of application Ser. No. 07/544,843, filed Jun. 27, 1990, now abandoned.

BACKGROUND OF THE INVENTION

1. Field of the Invention

This invention relates to an implant prosthesis adapted to construct artificial bones and artificial tooth for orthopedic surgery used for restoring the bone function and joint function of hands and feet lost by diseases and accidents or for restoring the artificial tooth root adapted for reconstruction of the tooth lost due to old age and diseases. This invention also relates to a method of producing the same.

2. Prior Art

In recent years there has been reported a remarkable development of implantology, and various artificial organs such as artificial heart, artificial blood vessel, artificial lungs play a brilliant role in medical circles.

Particularly, artificial bones for use in artificial joints for recovering the lost joint function are widely used, while the artificial root of a tooth is highlighted in the field of dental treatment.

Because endosseous type implant prosthesis of the kind described such as the artificial joint, artificial bone, artificial tooth root require high strength, stainless steel and cobalt-chromium alloy have conventionally been used for the implant prosthesis materials. But the problem arose that the metal material rusts within a living body to dissolve metallic ion to produce advserse effects on the bone cell and in the worst case the implant material may break.

In an attempt to solve the problem of affinity of this metal prosthetic material with the tissue of a living body, a ceramic material such as alumina has come to be introduced and has found its application in an artificial knee joint and the like. The ceramic material is excellent in its affinity with the bone tissue and is united into one body with the bone in the human body, with not always unexceptional cases of splended restoration in function. But when the material was used under the load of walking or the like, it failed to obtain sufficient fixation to the bone, with no small number of cases of loosening and revision or redoing. In an effort to solve the problem of endosseous fixation of the ceramic implant prosthesis material of the kind described above, coating of the implant with calcium phosphate based material by plasma spraying has been developed and is discussed in Japanese patent publication No. 46911/1984.

It is well known that calcium phosphate based materials (hereinafter referred to as apatite) such as hydroxyapatite, tricalcium phosphate are chemically united with bones and also a metal implant material having a coating applied thereover by thermal spraying is already commercially available. The above-disclosed art also uses thermal spraying of apatite or a mixture of apatite and ceramic powder onto the surface of the ceramic implant or forms a ceramic layer over the ceramic implant by thermal spraying and a further apatite coating thereover once more.

However, although the prior art mentioned above is an effective art, yet raises serious problems in point of practical application. One of the problems is concerned with the adhesive force of the apatite thermally sprayed layer relative to a foundation. According to the thermal spraying, as is generally the case, the spraying secures an adhesive force of the thermally sprayed layer by toughening the foundation by sandblasting. Namely, thermal spraying depends solely upon mechanical anchoring for the adhesive force of the thermally sprayed layer relative to the foundation, and accordingly, unless the foundation has a certain degree of irregularities on the surface thereof, the thermally sprayed layer cannot stick to the foundation. Although the artificial joint and bone are made of a high strength ceramic material such as alumina, zirconium dioxide, yet the mentioned ceramic materials are of high strengh and are at the same time very hard and it is difficult to roughen the surface of the ceramic material by use of sandblast. Also, the sandblast forcefully carried out cannot provide a sufficient degree of roughness and the thermal spraying of the apatite layer over the thus toughened surface cannot provide an adhesive force which can stand the use of the layer as an implant prosthesis.

On the other hand, the ceramic material is fragile and susceptible to scratches. Even if the scratches are small, they may cause a great reduction in the strength of the material. Sandblasting is an effective means for toughening the surface of a metal material which is a ductile material, but is a risky means which brings about reduced strength relative to the ceramic material. The same is also the case with means other than the blasting for forming a roughened surface. It is an established fact that the deflection strength of monocrystalline alumina is reduced to half or less by small scratches and toughening. The second problem of the prior art mentioned above is the disadvantages of reduction in the strength of the ceramic substrate of the kind thus described above.

SUMMARY OF THE INVENTION

The invention has for its object the solution of two problems relative to the conventional art and the development of a ceramic material having an apatite layer thermally sprayed thereover for practical use. According to the invention, there is provided an implant prosthesis excellent both in biocompatibility and prosthetic stability in a living body and which is increased in binding force, with no need of sandblasting effected, between the thermally sprayed apatite layer and the ceramic substrate by forming a glass layer in the form of an intermediate bonding layer between the thermally sprayed layer and the ceramic substrate.

A description will now be given below of the invention with reference to the accompanying drawing.

DETAILED DESCRIPTION OF THE INVENTION

Figure 1:
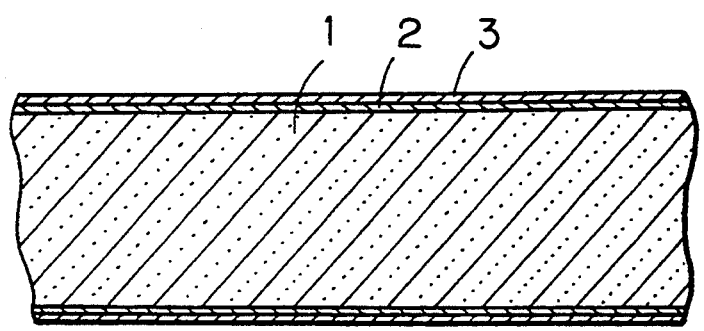
FIG. 1 is a sole view of the drawing showing an enlarged sectional view, partly broken, of an artificial bone according to the invention.

Generally speaking, the numeral 1 in the drawing designates an implant prosthesis substrate of ceramic material; 2 a thin glass layer used as an intermediate layer; and 3 designates a thermally sprayed layer made of calcium phosphate based material and laid over the glass layer 2. With particular reference to a manufacturing procedure for this structure, a glass slurry is applied over a ceramic substrate 1 such as of alumina, zirconium dioxide, and is fired at a temperature in the range of 900°~1300° C. to coat the substrate 1 with the glass layer 2. After the glass layer 2 is roughened by sandblasting, apatite is thermally sprayed over the toughened glass surface and the coated layer is fired at 600°~1100° C. to increase adhesion of the apatite layer 3 to the glass layer 2. Namely, during firing, the glass layer 2 passes in part through the pores in the apatite thermally sprayed layer to strenghen adhesive force of the apatite thermally sprayed layer relative-to the glass layer 2. In this manner, the apatite thermally sprayed layer 3 is increased in adhesive force. On the other hand, the ceramic substrate 1 is not subjected to direct toughening, and accordingly the substrate 1 is not reduced in strength. On the contrary, as will later be described, the implant substrate 1 of the invention is rendered higher in deflection strength than that of the prior art.

The important point worthy of attention in the invention is the coefficient of thermal expansion of glass forming the glass layer 2. In order to obtain a sufficient adhesive force of glass relative to the ceramic substrate 1, it is desirable that the coefficient of thermal expansion of glass be in the range of $3.0 \times 10^{-6}/°C. \sim 12.0 \times 10^{-6}/°C.$ Particularly, the coefficient of thermal expansion of glass is optimumly in the range of $4.0 \times 10^{-6}/°C. \sim 9.0 \times 10^{-6}/°C.$ relative to an alumina ceramic substrate.

Also, important is the thickness of the glass layer 2 to be coated and of the apatite thermally sprayed layer 3. The glass layer having a thickness less than 0.001 mm cannot give full play to its function as an intermediate layer, but conversely a glass layer having a thickness exceeding 2 mm is not suited for the implant material in point of dimensional restrictions. In the apatite thermally sprayed layer of 0.005 mm or less in thickness, the layer sinks into the glass layer and is embedded therein. On the other hand, the layer 3 which exceeds 1 mm in thickness is subject to inner rupture within the apatite thermally sprayed layer 3, hence unsuited for an implant material.

A description has been given above of the case wherein hydroxyapatite is use for the apatite thermally sprayed layer 3, but the use of calcium phosphate based material such as tricalcium phosphate could produce the same effect.

EMBODIMENTS

A detailed description will now be given below of preferred embodiments of the invention.

EXAMPLE 1

A silica based glass slurry was applied onto a monocrystalline alumina substrate of 23 mm in diameter and 1 mm in thickness, and after sufficient drying, was fired at 1100° C. for two hours. The surface of the glass layer was subjected to sandblasting in which alumina particles were used. The layer thus treated was cleaned well and dried. The layer was then coated with hydroxyapatite by flame spraying, thereafter fired at 900° C. for two hours to obtain a thermally sprayed layer. The glass layer obtained was about 20 μm in thickness and the apatite thermally sprayed layer was about 10 μm in thickness. Upon observation by electron microphotograph of crystalline structure on the surface of the above specimen, the apatite thermally sprayed layer was found to have been adhered firmly to the monocrystalline alumina substrate because the glass layer was interposed between the layer and the substrate.

Incidentally, as a contrast example 1, apatite was thermally sprayed over the monocrystalline alumina substrate equivalent to the above substrate with no glass coated layer interposed therebetween for coating the alumina substrate with an apatite layer. The adhesive force of the thermally sprayed layer relative to the alumina substrate was such a degree of adhesion as if the substrate were soiled with dust. The same result as that of Contrast Example 1 was obtained from Contrast Example 2 in which, after the substrate was sandblasted without coating of the glass layer, the apatite layer was thermally sprayed over the substrate. The adhesive force of the product obtained in Contrast Example 2 was such that touch by a finger on the surface of the apatite layer causes the layer to come off the substrate. Table 1 shows the result of adhesive force test.

TABLE 1

| Testing method | Substrate according to the example of the invention | Substrate according to Contrast Example 1 | Substrate according to Contrast Example 2 |
| --- | --- | --- | --- |
| Peeling-off | Not peeled off | Entirely peeled off | Partially peeled off (about 80%) |
| Scratching | Not peeled off | Entirely peeled off | Peeling-off observed in some cases |

Remarks:
Substrate according to Contrast Example 1 . . . thermally sprayed with neither glass layer nor sandblasting
Substrate according to Contrast Example 2 . . . thermally sprayed without glass layer but with sandblasting

Example 2

With respect to the middle of one side having an area of 5 mm×40 mm of a polycrystalline alumina substrate having a three-dimensional size of 5 mm×5 mm×40 mm, deflective strength was measured by use of a substrate coated with a glass layer by the same method as that in Example 1 and of a substrate coated with an apatite thermally sprayed layer by plasma spray coating and by use of a substrate, as a substrate in Contrast Example 3, coated with neither a glass layer nor with an apatite thermally sprayed layer. Recourse is had to JIS R1601 (testing method for bending strength of fine ceramics). The number of substrates used are five for each example. The test result is shown in Table 2.

TABLE 2

| Specimen | Substrate according to the invention | Substrate according to Contrast Example 3 |
| --- | --- | --- |
| No. 1 | 5591 | 4618 |
| No. 2 | 6423 | 4329 |
| No. 3 | 5812 | 4364 |
| No. 4 | 4707 | 4101 |
| No. 5 | 6454 | 4204 |
| Mean deflection strength | 5797.4 | 4322.8 |
| Standard deviation | 716.9 | 195.0 |

(unit kg/cm²)

As shown in Table 2, the implant prosthesis of the invention is higher in deflection strength by about 35% than the substrate in Contrast Example 3 having no coating spread thereover. This is thought to be the presence of a glass layer on the implant. The substrate in contrast Example 4 having an apatite thermally sprayed layer spread directly thereover with sandblast effected but without coating of the glass layer interposed between the implant and the glass coating was far lower in deflection strength than that in Example 3. Incidentally, it was ascertained that a zirconium dioxide ceramic substrate having an apatite thermally sprayed thereover was as high as the substrates in Examples 1 and 2 in the strength of adhesion of the apatite thermally sprayed layer to the substrate and also excellent in deflection strength.

Effects of Animal Experiment

An artificial tooth root of monocrystalline alumina ceramics adapted to be embedded in a bone was coated with a glass layer and an apatite thermally sprayed layer by the method in Example 1. The implant thus obtained was set in the mandible of a monkey. Three months have passed and monkey is still placed under observation and good fixation is confirmed.

As described above, the implant material of the invention has provided an implant prosthesis material far superior to the materials heretofore proposed by prior arts in that it is superior in biocompatibility and is increased in stability in a living body because the implant material is provided by coating the glass coated surface with calcium phosphate based hydroxyapatite, tricalcium phosphate by thermal spraying and thus because it has no fear of coming off and/or falling off the substrate and moreover of bringing about the reduced strength of the substrate.

I claim:
1. An implant prosthesis produced by the steps of:
   (a) providing a substrate of ceramic material;
   (b) coating the substrate with a thin glass layer, the thin glass layer defining a surface remote from the substrate;
   (c) roughening the surface of the thin glass layer remote from the substrate;
   (d) thermally spraying a layer of calcium phosphate-based material on the roughened surface of said glass layer; and
   (e) firing said layer of calcium phosphate based material at a temperature in the range of 600° to 1100° C.

2. An implant prosthesis according to claim 1, wherein said ceramic material is selected from the group consisting of monocrystalline alumina ceramics, polycrystalline alumina ceramics, zirconium dioxide ceramic, and said calcium phosphate-based material is hydroxyapatite or tricalcium phosphate.

3. An implant prosthesis according to claim 1, wherein the step of roughening the surface of the glass layer comprises the step of sandblasting the surface of the glass layer.

4. An implant prosthesis according to claim 3, further including, prior to step (d), the step of firing said glass layer at a temperature in the range of 900° to 1300° C.

5. An implant prosthesis according to claim 4, wherein said glass layer obtained in step (b) has a thermal expansion coefficient of from $4.0 \times 10^{-6}/°$ C. to $9.0 \times 10^{-6}/°$ C. and said ceramic material is alumina.

6. An implant prosthesis according to claim 1, further including, prior to step (d), the step of firing said glass layer at a temperature in the range of 900° to 130° C.

7. An implant prosthesis according to claim 1, wherein said glass layer obtained in step (b) has a thermal expansion coefficient of from $3.0 \times 10^{-6}/°$ C. to $12.0 \times 10^{-6}/°$ C.

8. An implant prosthesis according to claim 1, wherein said glass layer is 0,001–2 mm in thickness and said thermally sprayed layer is 0,005–1 mm in thickness.

* * * * *